United States Patent [19]
Martin

[11] Patent Number: 5,106,377
[45] Date of Patent: Apr. 21, 1992

[54] CHORION BIOPSY CATHETER

[75] Inventor: Geoffrey S. Martin, Mississauga, Canada

[73] Assignee: VAS-CATH Incorporation, Mississauga, Canada

[21] Appl. No.: 472,006

[22] Filed: Jan. 30, 1990

[30] Foreign Application Priority Data

Jan. 30, 1989 [CA] Canada ............... 589512-0

[51] Int. Cl.⁵ .............. A61M 5/178; A61M 25/00; A61B 10/00
[52] U.S. Cl. .................. 604/164; 604/170; 604/281; 604/282; 128/758
[58] Field of Search .............. 604/164-170, 604/19, 21, 27-35, 900, 280, 281-283, 93, 95, 264, 158, 159, 239; 128/766, 768, 767, 758

[56] References Cited

U.S. PATENT DOCUMENTS

| 1,900,006 | 7/1933 | Dozier | 604/170 |
| 1,906,678 | 5/1933 | Wappler | 604/170 |
| 2,118,631 | 5/1938 | Wappler | 604/170 |
| 3,777,743 | 12/1973 | Binard et al. | 128/760 |
| 3,889,657 | 6/1975 | Baumgarten | 128/758 |
| 4,033,331 | 7/1977 | Guss et al. | 604/281 |
| 4,563,181 | 1/1986 | Wijayarathra et al. | 604/280 |
| 4,627,444 | 12/1986 | Brooker | 128/760 |
| 4,747,827 | 5/1988 | Micek | 604/281 |
| 4,756,708 | 7/1988 | Martin | 604/283 |
| 4,834,709 | 5/1989 | Banning et al. | 604/281 |
| 4,834,726 | 5/1989 | Lambert | 604/281 |
| 5,047,018 | 9/1991 | Gay et al. | 604/165 |

Primary Examiner—C. Fred Rosenbaum
Assistant Examiner—Mark Bockelman
Attorney, Agent, or Firm—Rogers & Scott

[57] ABSTRACT

A catheter is provided for sampling, and particularly for sampling chorionic villi. The catheter has a cannula of a material opaque to ultrasound and having a distal portion capable of being curved manually into a desired curvature for use, and defining a lumen extending throughout the length of the cannula for containing a supple obturator to close the distal end of the lumen during insertion and to permit removal of the sample by applying a negative pressure to the proximal end of the catheter once the catheter is in position and the obturator removed.

2 Claims, 1 Drawing Sheet

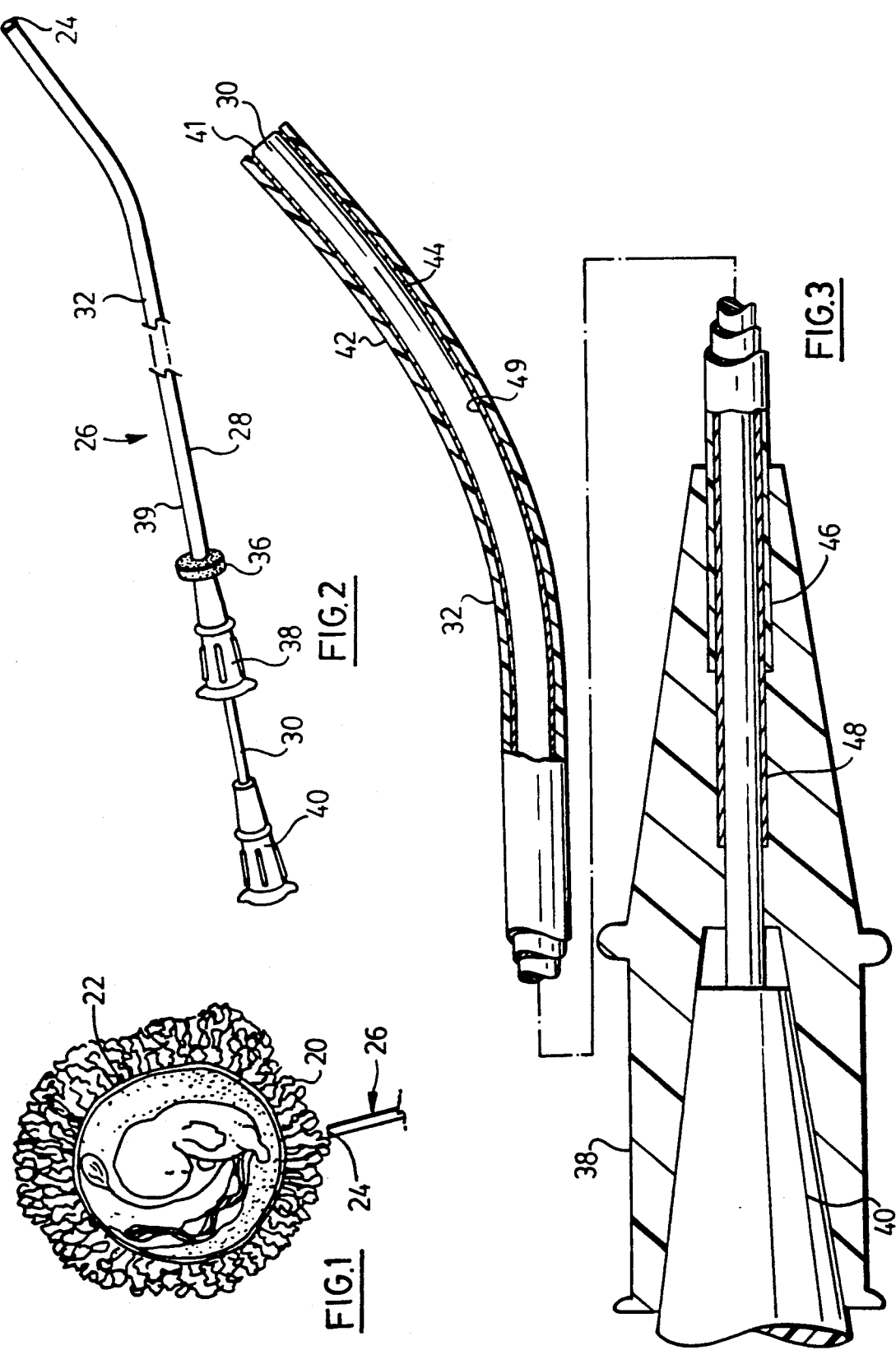

CHORION BIOPSY CATHETER

The present invention relates to biopsy catheters and particularly, but not exclusively, to catheters for taking biopsies from the chorionic membrane surrounding a seven to eight week old fetus, for subsequent analysis to determine the genetic health of the fetus. The invention will be described with exemplary reference to use in sampling chorionic villi.

BACKGROUND OF THE INVENTION

During pregnancy, early detection of fetal defects is important, especially to older women, many of whom would rather have an abortion than give birth to a baby with a defect such as Downs Syndrome. In any procedure for the detection of early fetal defects it is important that the procedure should involve a minimal risk of miscarriage or of inadvertently inducing abortion. In addition, the test should be performed as soon as possible in the pregnancy, because a decision to abort the pregnancy becomes increasingly difficult, both emotionally and physically with the passage of time. The fetal detection test should also minimize the risk of inadvertently inducing abortion.

Since the 1960's, pregnant women (usually over 35) who have been concerned about the possibility of bearing a child with birth defects, relied on a test called amniocentesis to determine the presence of birth defects. This procedure involves the use of a syringe or large needle to withdraw a small amount of fluid surrounding the fetus from which it can be determined whether defective chromosomes are present. This procedure is typically performed after the fourth month of pregnancy. At this stage the growth of the fetus is so far advanced that a decision to abort can involve significant physical and emotional problems. Investigations of this procedure have produced statistics supporting the suggestion that the procedure causes miscarriages in one of every two hundred women tested. From such investigations it is evidently desirable to be able to detect the presence of fetal defects earlier in the pregnancy and also to reduce the risk of causing a miscarriage or inadvertent abortion. Another problem with amniocentesis is that it takes two to four weeks to grow recovered cells in sufficient quantity for study and consequently even with the earliest possible test a fetus has to be 18 to 20 weeks advanced before this test will yield accurate results.

A procedure which has gained acceptance is Chorionic Villi Sampling (CVS). Chorionic villi are finger-like projections of tissue in the chorionic membrane which eventually forms the placenta. Chorionic villi are well developed around the seventh to eighth weeks of pregnancy. The object of this procedure is to remove, by vacuum, a sample of the villi and assay the sample to determine the genetic health of the fetus. A physician inserts a thin catheter (consisting of a cannula containing an obturator) through the vagina and cervix into the uterus ending at the chorion membrane. When the catheter tip is located on the villi, a source of negative pressure is coupled to the catheter to withdraw a sample of villi tissue for analysis. The advantages of this procedure over amniocentesis is that the biopsies or samples obtained provide enough tissue for analysis, which takes about ten days. Thus, early indications of fetal defects around the seventh to eighth week of pregnancy can be obtained.

To sample chorionic villi it is important that the catheter used is flexible to facilitate insertion yet is curved to conform to the anatomical configuration of the patient. The catheter should have sufficiently rigidity to be handled easily by the physician, and, in addition, once the catheter tip is located on the chorionic villi it is important that when the obturator is withdrawn, the cannula tip remains in the selected location for removing villi from this location in sufficient quantity for analysis. If the tip is moved by the action of withdrawing the obturator, there is a possibility of damage to the chorion membrane if the tip remains in contact, or alternatively the tip may move away from the villi so that the procedure will fail to collect a sample.

One type of existing catheter consists of a hollow flexible cannula and a 1.5 mm diameter flexible aluminum obturator which fits snugly in the cannula to facilitate inserting the cannula. In use, the physician slides the obturator into the cannula and then bends the resulting catheter to obtain the desired degree of bend for insertion. The catheter is then inserted to the desired location and finally the obturator is withdrawn. Although the aluminum obturator is flexible enough to be bent easily by hand, it inevitably retains sufficient rigidity in its bent position to tend to flex the curved portion of the cannula as the curved obturator is removed. As a result the cannula tip is commonly moved from the desired location where it was positioned before the obturator was removed. Apart from this pronounced possibility of tip displacement, it can be difficult to pass the curved obturator through the outer end fitting on the cannula.

Another form of catheter is produced by Downs Surgical plc of England. This product is available through subsidiaries in other countries and consists essentially of a malleable silver cannula which contains a flexible blunt stainless-steel obturator during insertion. The obturator supports the cannula to permit the cannula to be flexed without kinking thereby ensuring that the tubular cannula has internal continuity. The removal of the obturator will clearly affect the cannula because no matter how flexible the stainless-steel obturator is, it will have some stiffness and will affect the shape of the cannula as the obturator is removed so that the end of the cannula will inevitably be removed relative to the position in which it was placed when the obturator was contained in the cannula. Clearly this device also suffers from the aforementioned disadvantages. However it is even less desirable in that the necessary thin wall of the silver cannula has to result in a relatively sharp end which is undesirable in such a device.

Another catheter which uses an internal metallic obturator is designated Model "CV 2" by Lega International Manufacturing & Sales of Chicago, Toronto and Dusseldorf. In this case an aluminum obturator is contained in a flexible cannula of synthetic plastic material and the resulting catheter can be bent into the required shape. The obturator is then removed and of course, because of its strength relative to the plastic cannula, it will cause flexing and will have to be pulled quite firmly out of the cannula because the connections will tend to straighten the obturator.

It is clear from the foregoing that all prior art devices which use an obturator having greater stiffness than the cannula will suffer from the disadvantage of tip displacement when the obturator is removed. In an attempt to overcome this difficulty, a catheter with a preformed curvature was described in U.S. Pat. No. 4,756,708 to the present inventor and this patent issued on July 12, 1988. A precurved cannula received an obturator with a very flexible end which could extend to the end of the cannula to close the catheter during insertion and which could be removed without flexing the curved end portion of the cannula.

It has been found that the structure shown in this U.S. patent is entirely satisfactory in about 80 percent of its uses but that the preset curvature is not the required curvature in about 20 percent of the cases. It is therefore desirable to overcome this disadvantage and that of the other prior art structures by providing a catheter which will be satisfactory in all cases.

SUMMARY OF THE INVENTION

The present invention provides an improved biopsy catheter especially for use in Chorionic Villi Sampling (CVS) during the early stages of pregnancy. The preferred embodiment of catheter is for such use and is exemplary of other catheters which use the inventive concept.

The catheter is of a material opaque to ultrasound and having a distal portion capable of being curved manually into a desired curvature for use, and defining a lumen extending throughout the length of the catheter for containing a supple obturator to close the distal end of the lumen during insertion and to permit removal of the sample by applying a negative pressure to the proximal end of the catheter once the catheter is in position.

BRIEF DESCRIPTION OF THE DRAWINGS

FIG. 1 is a diagrammatic view of a fetus and shows a tip of a catheter next to the chorionic villi ready to withdraw a sample of the villi;

FIG. 2 is a perspective view of a preferred embodiment of a catheter with the obturator partially engaged in the catheter; and FIG. 3 is a side view, partly sectioned (and drawn to a larger scale) of parts of the catheter.

DESCRIPTION OF THE PREFERRED EMBODIMENT

Reference is first made to FIG. 1 which illustrates diagrammatically chorionic villi 20 of the chorionic membrane 22 and a forward or distal end 24 of a preferred form of catheter 26 according to the invention. The catheter is in position to withdraw samples of the finger-like villi. It is necessary to be able to position the end 24 using an obturator to occlude the opening in the end and then to remove the obturator while leaving the end in the same position. After such location, a vacuum is used of sufficient magnitude to draw part of the villi through the opening into the catheter, which is then withdrawn and the sample removed for analysis.

The structure of the catheter 26 is illustrated in FIG. 2 and shows a cannula 28 with an obturator 30 partially engaged. The body of the cannula (designated 32) typically has an outside diameter of 0.066 inches and is about 9 inches long. The body is shown curved ready for insertion of the catheter and terminates at the forward end 24 which defines the end opening having an internal diameter of about 0.040 inches. A rubber disk 36 is optionally mounted over the body of the catheter to facilitate handling of the cannula and as a means to set the depth of penetration if required. A first coupling in the form of a luer fitting 38 is attached to an outer or proximal end 39 of the body 32 to receive a second coupling which is also in the form of a luer fitting 40 on the obturator 30 for handling and for locating the obturator relative to the cannula during insertion. The fitting 38 also provides for attachment to a tube from a vacuum source for sampling after insertion and removal of the obturator.

The obturator 30 can be of any suitable synthetic plastic material such as polyurethane made to have a supple main portion which is proportioned to pass through the luer fitting 38 and engage snugly in the body 32 of the cannula with a distal end 41 of the obturator essentially flush with the end 24 when the fitting 40 is engaged in fitting 38. This is better seen in FIG. 3 where it will be noticed that the body 32 is of a compound construction consisting of an outer sleeve 42 preferably of Nylon and containing an inner tube 44 which is of a thin wall stainless steel typically having an internal diameter of 0.040 inches and an external diameter of 0.050 inches. The stainless steel is fully annealed to minimise stiffness and the outer sleeve is in intimate contact with the inner tube 44. The sleeve 42 and tube 44 terminate at respective proximal end portions 46, 48 set in the luer fitting 38 during injection moulding of this Nylon fitting so that the sleeve and tube are held firmly in relation to one another to prevent possible longitudinal relative movement and to define a lumen 49.

At the distal end of the body 32, the sleeve 42 terminates outside the distal extremity of the tube 44 to provide protection for the tube which of course is of stainless-steel and therefore quite sharp because of its thin wall. The obturator 30 is preferably brought level with the sleeve 42 as a result of the location of the luer fitting 40 in the luer fitting 38.

It will be evident from this arrangement that the user can make adjustments to the shape of the catheter after assembling the obturator in the cannula. This is done manually and the Nylon sleeve 42 provides support for the thin walled tube 44 circumferentially of the tube at locations where bending forces are applied to thereby minimize the risk of collapsing the tube locally under the influence of these bending forces. The obturator will assist in this simply because it is a snug fit within the tube but will have no measurable resistance to bending due to the supple nature of the obturator. The structure allows the user to shape the catheter as required before insertion.

After the catheter has been positioned using ultrasonic techniques, and because the cannula is opaque to these techniques, the tip 24 can be positioned as shown in FIG. 1 relative to the villi. Once the catheter is in the required position, the obturator can be withdrawn and, because it is supple, it will have no effect on the much stronger cannula so that the curved part of the cannula prepared before use will retain this shape and the tip 24 will not move as a result of the withdrawal of the obturator. This permits the user to position the tip 24 accurately knowing that it will remain there when the obturator is removed. Subsequent application of vacuum will collect samples of villi at this location.

Although the invention has been described with reference to the collection of villi, it will be clear that the principles can be applied to a variety of catheters requiring shaping before use. The inherent stiffness of the cannula body 32 ensures that the shape will be retained while the much weaker and supple obturator is removed. These and other aspects of the invention are within the scope of the claims.

I claim:

1. A catheter for use in collecting samples from the chorionic membrane at a predetermined location, the catheter comprising:

a cannula having a proximal end, first coupling means at the proximal end, an open distal end, and an elongate tubular body having an inner tube of thin walled metal and an outer sleeve of a soft synthetic plastics material, the outer sleeve projecting slightly beyond the inner tube at said distal end and the tubular body extending from the coupling means to the open distal end and defining with the coupling means a lumen extending throughout the length of the cannula, the body being deformable manually into a preselected curvature as required to match body contours prevailing where the catheter is to be inserted; and an elongate obturator of supple material proportioned to close the open distal end of the lumen during insertion and being sufficient supple to have no measurable effect on said curvature of the body when the obturator is withdrawn from the cannula with the cannula in position to collect said samples so that the distal end of the catheter remains in position relative to the chorionic membrane.

2. A catheter as claimed in claim 1 in which the obturator includes second coupling means engageable with said first coupling means to locate the distal end of the obturator at the distal end of the body.

* * * * *